(12) United States Patent
Johnson et al.

(10) Patent No.: US 6,599,913 B1
(45) Date of Patent: Jul. 29, 2003

(54) TREATING ALLERGIC AND INFLAMMATORY CONDITIONS

(75) Inventors: William W. Johnson, Sparta, NJ (US); Er-Jia Wang, Sparta, NJ (US); Christopher Casciano, Newton, NJ (US); Robert P. Clement, Morris Plains, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/177,271

(22) Filed: Jun. 21, 2002

Related U.S. Application Data

(60) Provisional application No. 60/302,132, filed on Jun. 29, 2001.

(51) Int. Cl.⁷ .......................................... A61K 31/473
(52) U.S. Cl. ..................................................... 514/290
(58) Field of Search .......................................... 514/290

(56) References Cited

U.S. PATENT DOCUMENTS

| | | | | |
|---|---|---|---|---|
| 4,282,233 A | * | 8/1981 | Vilani .................... | 514/253.05 |
| 4,659,716 A | * | 4/1987 | Villani et al. ................ | 514/290 |
| 6,140,337 A | * | 10/2000 | Binder et al. ................ | 514/290 |
| 6,265,414 B1 | * | 7/2001 | Harris et al. ................ | 514/290 |
| 6,423,721 B1 | * | 7/2002 | Harris et al. ................ | 514/290 |
| 6,432,972 B2 | * | 8/2002 | Salmun et al. ............... | 514/291 |
| 6,451,815 B1 | | 9/2002 | Hwang et al. ............... | 514/317 |
| 2001/0006971 A1 | * | 7/2001 | Kreutner ..................... | 514/290 |
| 2002/0019409 A1 | * | 2/2002 | Affrime et al. ............. | 514/290 |

* cited by examiner

Primary Examiner—James H Reamer
(74) Attorney, Agent, or Firm—Robert J. Lipka

(57) ABSTRACT

A method of treating and/or preventing allergic and inflammatory conditions of the skin or airway passages in a human in need of such treating and/or preventing which comprises administering to said human an effective amount of a nonsedating antihistamine for such treating and/or preventing while avoiding the side effects associated with other nonsedating antihistamines that bind to the P-glycoprotein pump and/or the organic anion transport polypeptide pump is disclosed.

67 Claims, 4 Drawing Sheets

TREATING ALLERGIC AND INFLAMMATORY CONDITIONS

This application claims formal benefit of priority to U.S. Provisional Patent Application Serial No. 60/302,132, filed Jun. 29, 2001.

BACKGROUND OF THE INVENTION

Loratadine is disclosed in U.S. Pat. No. 4,282,233 as a non-sedating antihistamine useful for treating allergic reactions in animals including humans. See also Claritin brand of Loratadine. Product Information Sheet, dated 1/99. Desloratadine is disclosed in U.S. Pat. No. 4,659,716 as a non-sedating antihistamine.

Histamine $H_1$-receptor antagonists are effective first-line therapeutic agents in the management of allergic rhinitis, a condition affecting approximately 45 million Americans with a trend toward a larger afflicted population. Due to the high incidence of allergic rhinitis across the full range of the population, antihistamines are often administered concurrently with other drugs. Because drug disposition and exposure can drastically change when a co-administered drug inhibits an avenue of elimination or disposition, e.g., a drug/drug interaction, the elevated exposure to one or more drugs can lead to potentially grave consequences.

Mammalian cells possess a natural battery of defense mechanisms against xenobiotic assault. A particular class of proteins actively transports an extensive array of structurally unrelated large lipophilic compounds from the cell, providing what is often known as multiple drug resistance (MDR). Multidrug resistance is characterized by active efflux or pumping of xenobiotics and pharmaceuticals via transmembrane proteins acting as hydrophobic "vacuum cleaners." The protein product of the MDR1 gene encodes a 170 kD integral plasma membrane phosphorylated glycoprotein, P-glycoprotein (P-gp), which is the best known and most extensively studied among these transporters and thus far appears to have the largest substrate list. The gross structural features of P-gp appear to be shared by a large family of membrane transporters known as ATP-binding cassette (ABC) transporters, which evidently act as ATP-driven pumps that remove xenobiotics from the interior of cells. Expression of P-gp in normal human tissues, particularly within the cellular membranes of the gastrointestinal tract, liver, blood-brain barrier, adrenals, and kidneys, suggests that the protein plays a role in cellular protection as well as in secretion. While the primary function of this protein is unknown, its ability to confer resistance to a wide variety of structurally and chemically unrelated compounds remains impressive. Indeed, the substrate list for this transporter reveals that P-gp shares a similar tolerance or acceptance as cytochrome P450 3A4 (CYP3A4), the predominant intestinal and hepatic cytochrome P450 oxygenase enzyme, and may even prove to be more extensive in its substrate recognition and as an avenue of drug elimination.

Among the more grave examples of clinical drug interactions are the $H_1$-receptor antagonist terfenadine with ketoconazole, as well as simvastatin with itraconazole and mibefradil; all are reportedly substrates/inhibitors of P-gp. Another $H_1$-receptor antagonist, fexofenadine, also reportedly interacts with erythromycin and ketoconazole. A report implicates active transporters as a major factor in the disposition of fexofenadine. Cvetkovic M., et al., *Drug Metab Dispos* 1999, Aug;27(8):866–71. Additionally, P-gp polymorphisms may cause wide-ranging reactions to treatment with P-gp substrates. If a polymorphic gene product of MDR1 has inferior selectivity toward a therapy, increased systemic exposure to that erstwhile P-gp substrate could be expected. Decleves X., et al., *Hum Mutat* 15:486.

At therapeutically effective doses, desloratadine was surprisingly found to not detectably bind to the P-gp protein. Also, in clinical studies, desloratadine pharmacokinetics were minimally affected by coadministration of grapefruit juice, which is known to alter drug transporter function.

The molecular mechanism underlying the hepatic uptake of organic anions has been significantly elucidated. Meier, et al., *Hepatology*, 1997 26(6):1667–77. The organic anion transport polypeptide 1 (OATP1) is a $Na^+$- and ATP-independent transporter localized to the basolateral membrane of hepatocytes (as well as cells in other tissues), where it plays a major role in uptake of a variety of structurally unrelated anionic, neutral, and even some cationic compounds from the blood into the cell. Ibid. OATP1 mediates uptake of a variety of amphipathic organic anions in exchange for $HCO_3^-$ and/or GSH and has been detected in the cells of kidney, liver, brain, lung, and muscle tissue. OATP1 has been demonstrated to transport bromosulfophthalein (BSP), bile acids, anionic steroid conjugates, neutral steroids, and other drugs. The inhibition of OATP1 function results in decreased exposure of substrates to cytosol and hence tissue.

The human OATP uptake antiport transporter has been shown to effect the disposition of fexofenadine. Cvetkovic M, et al., *Drug Metab Dispos* 1999, Aug;27(8):866–71. This report shows results from cells transfected with an OATP clone given by the University Hospital, Zurich, Switzerland. Using monolayers of the transfected cells and parent cells as controls, the rate of uptake was measured over a range of [$^{14}$C]fexofenadine concentrations. By analyzing the hyperbolic saturation curve a $K_m$ of 6.4±2.2 $\mu$M and a $V_{max}$ of 58 pmol/mg protein·min was determined and this was an efficiency of transport ranking high among tested substrates. Ibid. Additionally, the researchers were able to show significant inhibition of fexofenadine uptake by the drugs ritonavir, saquinavir, and lovastatin, and some other drugs.

Many food constituents (polyphenols and flavonoids) can directly effect the function of this uptake transporter. It is known that grapefruit juice and a coumarin constituent of grapefruit juice can have an effect on human OATP1. Additionally, grapefruit juice at 5% inhibited about 90% of human OATP1 mediated fexofenadine uptake and a major coumarin constituent of grapefruit juice inhibited rat oatp1 with an $IC_{50}$<1 $\mu$M. Dresser G. K., *Drug Met Reviews*, 2000, 32 (s2):193. This impedance can be predicted to cause clinical effects on fexofenadine.

As a substrate of transporters that is not metabolized by CYP enzymes, fexofenadine is commonly used as a probe of drug transporter function. In vitro and in vivo studies have shown that fexofenadine pharmacokinetics are dependent upon drug transporters: fexofenadine AUC is increase. 5- to 9-fold in mdr1 null (-l-) mice, which are devoid of P-gp activity. Murray, 2001 SCI-1124-01/EAS Abstract 4/01. Consequently, substances that alter the function of these transporters by decreasing or increasing their activity have the potential to alter the clinical safety and efficacy profiles of other P-gp/OATP substrates. Ibid.

Clinical studies have shown that consumption of such common foods as grapefruit juice, apple juice, and orange juice decrease fexofenadine AUC by 30% to 77%; inhibition of OATP-mediated drug uptake and/or induction of active drug efflux appears to be responsible. Ibid. Agents that modify P-gp/OATP activity-including St. John's Wort, ketoconazole, and erythromycin, and terfenadine have also reportedly been shown in clinical trials to alter the bioavailability of fexofenadine. Ibid.

A recent clinical interaction study performed has produced a reduction in fexofenadine exposure when co-administered with grapefruit juice. In this four-way crossover study grapefruit juice reduced both $C_{max}$ and AUC of fexofenadine by 30%. Cohen A., et al., (Protocol No. P01380), SPRI Clinical Pharmacology Study, P01380. This result is consistent with the inhibition of OATP1 mediated uptake of fexofenadine since constituents in grapefruit are known to be potent inhibitors of this transporter. This result was corroborated and extended in a 5 way, cross-over study in which the reduction of fexofenadine bioavailability was also observed with orange, apple and grapefruit juice. Bailey D. G., et al., Clin Pharn Ther 2001 69(2):21 (Abs PI-82). Apples and oranges are known to contain various polyphenolics and flavonoids that inhibit some transporters. The mechanism of this effect on absorption was further elucidated by studies with mdr1a/1b-deficient (-l-) mice and in vitro with cells expressing heterologous rat Oatp3. The co-administration of grapefruit or orange juice with fexofenadine in the mdr knockout mice lacking P-gp reduced fexofenadine AUC. The Oatp3 in vitro experiments showed that fexofenadine is a substrate of this uptake transporter with a $K_m$ of 36 $\mu$M. Since this transporter was shown to be inhibited by grapefruit juice, grapefruit constituents, and orange juice these observations indicate the importance of OATP uptake transport to the disposition of fexofenadine.

A further example that may exemplify the OATP transporter mechanism of interaction is the recently described suppressed exposure to fexofenadine when co-administered with rifampin. Hamman M. A., et al., Clin Pharmacol Ther2001 69(3):114–21. Fexofenadine $C_{max}$ was reduced about 35–50%; oral clearance is significantly increased. Although they did not determine the mechanism, it is probably inhibition of OATP function or induction of export transporter (ABC transporter). Rifampin is well known to induce (elevate production) xenobiotic enzymes, yet it is also an inhibitor of OATP1 and OATP2. This serves both as a further example supplementing those noted above, as well as a tool for further experiments.

The clinical effect of dietary salt on the bioavailability of fexofenadine deserves special study. Since dietary salt significantly lowers the AUC (~33%) and $C_{max}$ (~33%) of fexofenadine and OATP is driven by counter-transport of a small anion the observed effect might be mediated by this uptake transporter. Dresser, et al., Clin Pharm Ther 2001, 69 (2): 23 (Abs PI-88). Additionally, ABC transporter gene expression has been shown to be modulated by a high salt diet in rats. Another very intriguing clinical interaction is the suppressed exposure of fexofenadine caused by St. John's Wort. Dresser, et al., Clin Pharm Ther 2001, 69 (2): 23 (Abs PI-90). Pre-administration of St. John's Wort to 10 healthy volunteers also caused a dramatic decrease in fexofenadine AUC (~50%). Ibid. Since apple juice and other citrus fruit and St. John's Wort both contain quercetin and chlorogenic acid, the OATP transporter, which is affected by various citrus constituents, deserves consideration as the potential mediator of this clinical interaction. However, another lab has observed a significant increase in fexofenadine $C_{max}$ after acute single dose (900 mg) of St. John's Wort, but no significant effect after 14 days of dosing (300 mg). Hamman, MA., et al., Clin Pharmacol Ther2001 69(2):53 (Abs PII-83). This may be caused by inhibition of an efflux transporter (ABC transporter) at the single acute dose and competing effects at the chronic dose.

In summary, the OATP uptake transporters are believed to be critical to fexofenadine disposition and bioavailbilty. Furthermore, the many other diverse substrates are causing decreased exposure of fexofenadine via this recently appreciated active transporter.

Potential drug interactions with fexofenadine via this avenue (OATP1) could include such commonly used pharmaceuticals as lovastatin, atorvastatin, simvastatin, saquinavir, ritonavir, quinidine, Cvetkovic M., et al., Drug Metab Dispos 1999, Aug;27(8):866–71, and pravastatin, Hsiang B., et al., J Biol Chem 1999, 274(52):37161–37168. Interactions would also likely be possible with corticosterone, Kanai N., et al., Am J Physiol 1996, 270(2):F319–325, dexamethasone, cortisol and aldosterone, Bossuyt X., et al., JPET 1996, 276:891–896, dehydroepiandrosterone, Kullak-Ublick G-A, , et al., FEBS Lett 1998 424:173–176, ibuprofen, Kouzuki H., et al., JPET 1999 288:627–634, indomethacin, Kouzuki, H , et al., JPET 2000 292:505–511, APD-ajmalinium (cationic derivative of the antiarrhythmic compound N-propylajmaline), Bossuyt X., et al, JPET 1996, 276:891–896.; and Meier, et al, Hepatology, 1997 26(6):1667–77, peptidomimetics and many others, Meier, et al., Hepatology, 1997 26(6):1667–77.

Persuasive in vitro evidence for a selective mechanism of interaction has been reported for some of these compounds. Pravastatin reportedly significantly interacts with rat OATP1 and simvastatin, lovastatin, and atorvastatin reportedly effectively inhibit rat OATP1 at 50 $\mu$M. Rat OATP1 reportedly minimally affects ibuprofen uptake. Corticosterone sulfate reportedly effectively inhibits rat OATP1 at 10 $\mu$M (some other steroids include: dehydroepiandrosterone and aldosterone). Ritonavir and saquinavir (HIV therapy protease inhibitors) reportedly effectively inhibit human OATP1 at 10 $\mu$M. Lovastatin reportedly effectively inhibits human OATP1 at 10 $\mu$M. Quinidine reportedly moderately inhibits human OATP1 at 10 $\mu$M and strongly at 100 $\mu$M. Of note, human OATP2 reportedly interacts with all of the statins. Additionally, rat OATP reportedly transports APD-ajmalinium, a permanently cationic derivative of the antiarrhythmic compound N-propylajmaline. Of these, lovastatin, saquinavir, ritonavir, and corticosterone (possibly, quinidine, APD-ajmalinium or pravastatin) should be most likely to result in a clinically significant drug interaction.

Drug transporters can have complex effects on the bioavailability of even negligibly metabolized drugs. Accordingly, there exists a need for a method of treating allergic and inflammatory conditions while avoiding the potential concomitant interaction with the OATP and P-gp enzyme systems.

SUMMARY OF THE INVENTION

Accordingly, there is disclosed a method treating and/or preventing allergic and inflammatory conditions of the skin or airway passages in a human in need of such treating and/or preventing which comprises administering to said human an effective amount of a nonsedating antihistamine for such treating and/or preventing while avoiding the side effects associated with other nonsedating antihistamines that bind to the P-glycoprotein pump and/or the organic anion transport polypeptide pump.

Also disclosed is a method treating and/or preventing allergic and inflammatory conditions of the skin or airway passages in a human of 12 years and older in need of such treating and/or preventing which comprises administering to said human an effective amount of a nonsedating antihistamine sufficient for such treating and/or preventing in the absence of the side effects associated with other nonsedating antihistamines that bind to the P-glycoprotein pump or the organic anion transport polypeptide pump.

Also disclosed is a method of treating and/or preventing seasonal or perennial allergic rhinitis in a human in need of such treating and/or preventing which comprises administering to said human an effective amount of desloratadine for such treating and/or preventing while avoiding the side effects associated with other nonsedating antihistamines that bind to the P-glycoprotein pump and/or the organic anion transport polypeptide pump.

Also disclosed is a method of treating and/or preventing atopic dermatitis or urticaria in a human in need of such treating and/or preventing which comprises administering to said human an effective amount of desloratadine for such treating and/or preventing while avoiding the side effects associated with other nonsedating antihistamines that bind to the P-glycoprotein pump and/or the organic anion transport polypeptide pump.

Also disclosed is a method of treating and/or preventing allergic asthma in a human in need of such treating and/or preventing which comprises administering to said human an effective amount of desloratadine for such treating and/or preventing while avoiding the side effects associated with other nonsedating antihistamines that bind to the P-glycoprotein pump and/or the organic anion transport polypeptide pump.

DETAILED DESCRIPTION OF INVENTION

Figure 1:
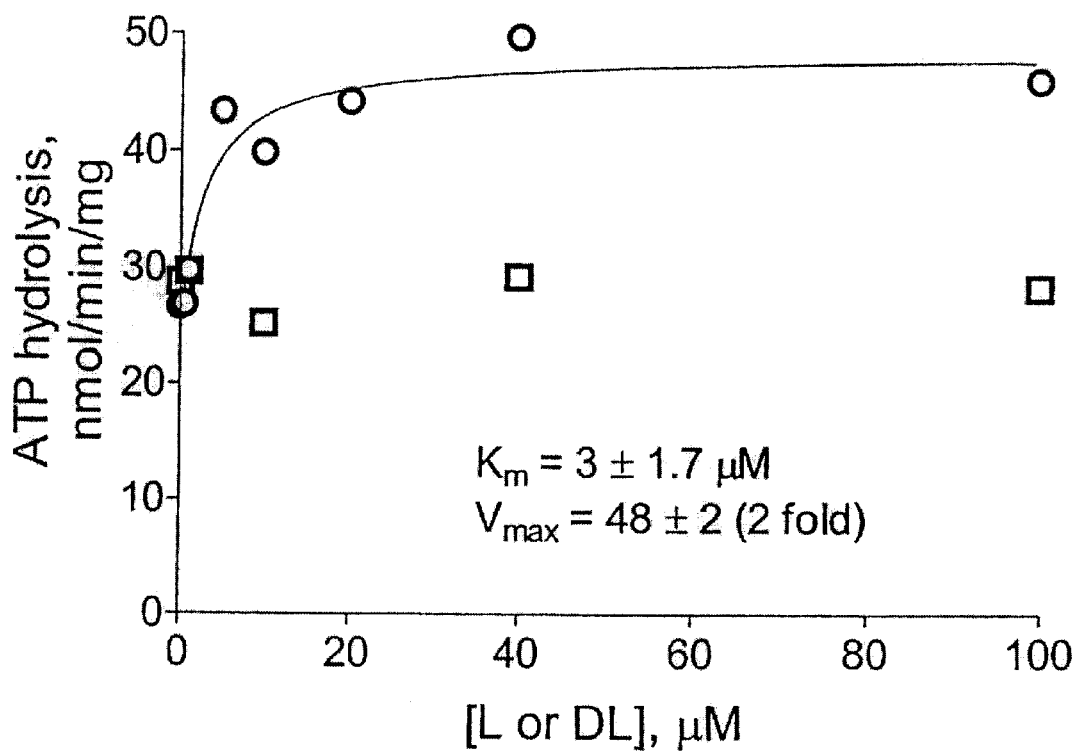
FIG. 1 depicts the inhibition of function of daunoribicin relative to verapamil and cyclosporine A.

The phrase "allergic and inflammatory conditions of the skin or airway passages" is meant those allergic and inflammatory conditions and symptoms found on the skin and in the upper and lower airway passages from the nose to the lungs. Typical allergic and inflammatory conditions of the skin or upper and lower airway passages include seasonal and perennial allergic rhinitis, non-allergic rhinitis, asthma including allergic and non-allergic asthma, sinusitis, colds (in combination with a NSAID, e.g., aspirin ibuprofen or APAP) and/or a decongestant e.g. pseudoephedrine), dermatitis, especially allergic and atopic dermatitis, and urticaria and symptomatic dermographism as well as retinophathy, and small vessel diseases, associated with diabetes mellitus.

The term "a human of 12 years and older" as used herein means a male or female pediatric subject equal to, or greater than 12 years of age to less than 18 years of age and adults of 18 years of age and older.

The amount of desloratadine effective for treating or preventing allergic and inflammatory conditions of the skin or airway passages will vary with the body weight and severity of the allergic and inflammatory condition of the patient. Typically, the amount of desloratadine effective for treating or preventing such allergic and inflammatory conditions in an adult human of 12 years of age and older is in the range of about 2.5 mg/day to about 20 mg/day, or about 5 mg/day to about 15 mg/day, or about 5 mg/day to about 10 mg/day, more preferably about 5 mg/day to about 7.5 mg/day, and most preferably about 5 mg/day in single or divided doses, e.g., 2.5 mg twice a day, i.e., 2×2.5 mg/day, or a single dose of 5 mg/day.

Surprisingly, at resulting plasma concentrations, it was found that desloratadine did not significantly bind to or inhibit either the P-gp pump, and clinical observations of in vivo test data indicate that desloratadine does not significantly bind to or inhibit the OATP pump as well, which was unexpected to one of ordinary skill in the art.

In the present invention, there is provided a safe and effective method of treating and/or preventing allergic and inflammatory conditions of the skin or upper and lower airway passages, e.g. seasonal allergic rhinitis, perennial allergic rhinitis, or chronic idopathic urticaria, in a human more 12 years old, by administering an amount of desloratadine, e.g., 2×2.5 mg or 5 mg/day desloratadine in the range of about 3.2 ng/mL to about 5.0 ng/mL.

Desloratadine is a non-sedating long acting histamine antagonist with potent selective peripheral $H_1$-receptor antagonist activity. Following oral administration, loratadine is rapidly metabolized to descarboethoxyloratadine or desloratadine, a pharmacologically active metabolite. In vitro and in vivo animal pharmacology studies have been conducted to assess various pharmacodynamic effects of desloratadine and loratadine. In assessing antihistamine activity in mice (comparison of $ED_{50}$ value), desloratadine was relatively free of producing alterations in behavior alterations in behavior, neurologic or autonomic function. The potential for desloratadine or loratadine to occupy brain $H_1$-receptors was assessed in guinea pigs following i.p. administration and results suggest poor access to central histamine receptors for desloratadine or loratadine.

The in vivo studies also suggest that an inhibitory effect of desloratadine on allergic bronchospasm and cough can also be expected.

The clinical efficacy and safety of desloratadine has been documented in over 3,200 seasonal allergic rhinitis patients in 4 double-blinded, randomized clinical trials. The results of these clinical studies demonstrated the efficacy of desloratadine in the treatment of adult and adolescent patients with seasonal rhinitis.

Efficacy endpoints in all the studies were Total Symptom Score, Total Nasal Symptom Score, Total Non-nasal Symptom Score, and Health Quality of Life (HQOL) analysis in efficacy trials. Desloratadine (5 mg once daily) significantly reduced the total symptom scores (the sum of individual scores for rhinorrhea, sneezing, congestion/stuffiness, nasal itching, itchy/burning eyes, tearing, ocular redness, and itchy ears/palate). Desloratadine (5 mg) was significantly ($p<0.01$) more effective than placebo in reducing nasal symptoms. An important efficacy endpoint analyzed in the desloratadine studies is the AM NOW total symptom score. This parameter measures the total symptom relief by the patient after 24 hours before taking the next day dose. Statistically significant ($p<0.05$) reductions were maintained for the full 24 hour dosing interval over the entire 5 mg to 20 mg dosage range There were no significant differences in the effectiveness of desloratadine (over the entire 5 mg to 20 mg dosage range) across subgroups of patients defined by gender, age, or race. Desloratadine is particularly useful for the treatment and prevention of the nasal (stuffiness/congestion, rhinorrhea, nasal itching, sneezing) and non-nasal (itchy/burning eyes, tearing/watery eyes, redness of the eyes, itching of the ears/palate) symptoms of seasonal and perennial allergic rhinitis, including nasal congestion, in patients in need of such treating and/ or preventing.

Desloratadine is also useful for the treatment of chronic idiopathic urticaria. Oral administration of desloratadine significantly reduced the severity of pruritus, number of hives and size of largest hive, total symptom score, interference with sleep and the interference with daily activities. Symptoms of chronic idiopathic urticaria were reduced following the first dose of a 5 mg desloratadine tablet and maintained for a full 24 hour dosing interval.

U.S. Pat. No. 4,659,716 discloses methods of making desloratadine, pharmaceutical compositions containing it and methods of using desloratadine and pharmaceutical compositions containing it to treat allergic reaction in mammals.

U.S. Pat. No. 5,595,997 discloses pharmaceutical compositions containing desloratadine and methods of using desloratadine for treating and preventing various disease states, e.g., allergic rhinitis.

U.S. Pat. No. 4,804,666 discloses 3-OH desloratadine pharmaceutical compositions containing desloratadine and methods of using the allergy in a mammal.

Desloratadine, 3-OH desloratadine and 3-OH desloratadine glucuronide are available from Schering Corporation, Kenilworth, N.J.

The pharmaceutical compositions of desloratadine can be adapted for any mode of administration e.g., for oral, parenteral, e.g., subcutaneous ("SC"), intramuscular ("IM"), and intraperitoneal ("IP"), topical or vaginal administration or by inhalation (orally or intranasally). Preferably desloratadine is administered orally.

Such pharmaceutical compositions may be formulated by combining desloratadine or an equivalent amount of a pharmaceutically acceptable salt thereof with a suitable, inert, pharmaceutically acceptable carrier or diluent that may be either solid or liquid. Desloratadine may be converted into the pharmaceutically acceptable acid addition salts by admixing it with an equivalent amount of a pharmaceutically acceptable acid. Typically suitable pharmaceutically aceptable acids include the mineral acids, e.g., $HNO_3$, $H_2SO_4$, $H_3PO_4$, HCl, HBr, organic acids, including, but not limited to, acetic, trifluoroacetic, propionic, lactic, maleic, succinic, tartaric, glucuronic and citric acids as well as alkyl or arylsulfonic acids, such as p-toluenesulfonic acid, 2-naphthalenesulfonic acid, or methanesulfonic acid. The preferred pharmaceutically acceptable salts are trifluoroacetate, tosylate, mesylate, and chloride. Desloratadine is more stable as the free base than as an acid addition salt and the use of the desloratadine free base in pharmaceutical compositions of the present invention is more preferred.

Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa. The preferred tablet formulations are made in accordance with the procedures of U.S. Pat. No. 6,100,274.

Liquid form preparations include solutions, suspensions and emulsions. As an example may be mentioned water or water-propylene glycol solutions for parenteral injection. Solid form preparations may be converted into liquid preparations shortly before use for either oral or administration. Parenteral forms to be injected intravenously, intramuscularly or subcutaneously are usually in the form of sterile solutions and may contain tonicity agents (salts or glucose), and buffers. Opacifiers may be included in oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g., nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in a unit dosage form. In such form, the preparation is subdivided into suitably sized unit doses containing appropriate quantities of the active component, e.g., an effective amount to achieve the desired purpose.

Further, desloratadine may be administered as a syrup, tablet, rapidly disintegrating tablet or reditab e.g., such as one that disintegrates in the mouth within seconds of placement on the tongue, or as an extended release formulation of desloratadine in association with therapeutically effective amounts (12 or 24 hour)of an upper airway passage decongestant including, but not limited to phenylephedrine and pseudoephedrine phenylpropanolamine or pharmaceutically acceptable salts thereof, in accordance with the dosing levels known to those skilled in the art and as described in the *Physicians' Desk Reference*. The use of pseudoephedrine HCl or pseudoephedrine sulfate is preferred.

The present invention provides methods and pharmaceutical compositions that are useful for treatment of allergic and/or inflammatory conditions of the skin (e.g. urticaria) and the upper and lower airway passages including the nasal and non-nasal symptoms of seasonal allergic rhinitis including nasal congestion in a patient in need of such treating. The precise dosage and dosage regimen may be varied by the attending clinician in view of the teachings herein depending upon the requirements of the patient, e.g., the patient's weight and the severity of the allergic and/or inflammatory condition being treated. Determination of the proper dosage and dosage regimen for a particular patient will be within the skill of the attending clinician. The preferred amount of desloratadine which may be delivered by any appropiate pharmaceutical composition is about 5 mg/day or 2.5 mg/twice a day. In accordance with the present invention, about 5 mg of desloratadine is administered once a day for about 10 days to a human of 12 years and older having, for example, the nasal and non-nasal symptoms of seasonal and perennial allergic rhinitis and/or the symptoms of chronic idiopathic urticaria, or other histamine mediated topical disorders. While we have hereinabove presented a number of preferred embodiments of this invention by way of example, it is apparent that the scope of the invention is to be defined by the scope of the appended claims.

The invention will be further described by reference to the following study. The purpose of this study was to determine, using two different methods, whether the nonsedating antihistamine loratadine and its active metabolite desloratadine interact with P-gp. MDR cells presenting human P-gp were incubated with the fluorescent P-gp substrate daunorubicin (DNR) with or without loratadine, desloratadine, and several positive controls. The $IC_{50}$ of loratadine (~11 µM) was ~160 times the maximum observed plasma concentration ($C_{max}$) following a dose of 10 mg. The $IC_{50}$ of desloratadine (~43 µM) was ~880 times the $C_{max}$ following a dose of 5 mg. The positive control, cyclosporin A, had an $IC_{50}$ of ~1 µM. ATP hydrolysis activity was measured in the membrane fraction prepared from MDR cells presenting P-gp, which were exposed to various concentrations of test compounds. Known substrates of P-gp demonstrated clear, repeatable, concentration-dependent increases in ATP hydrolysis activity. Loratadine caused an increase in ATPase activity above basal levels. Loratadine had a $V_{max}$ about 200% basal activity and $K_m$ of ~3 µm for P-gp. In contrast, desloratadine had no significant effect on baseline ATP hydrolysis. Loratadine inhibited human P-gp much less than verapamil or cyclosporin A. Desloratadine inhibited human P-gp significantly less than loratadine (4×). Desloratadine therefore is not a significant inhibitor of P-gp and should not cause clinical drug interactions with agents that are P-gp -substrates.

This report quantifies the interactions of loratadine and its active metabolite desloratadine with the substrate binding site of the ubiquitous ABC transporter, P-gp, using two different methods. Desloratadine has significantly less potential for interaction with P-gp than the most commonly prescribed antihistamine, loratadine—an agent known for its safety profile.

MATERIALS AND METHODS

Loratadine and desloratadine were from Schering-Plough compound resources. Daunorubicin (DNR), verapamil, colchicine, cyclosporin A, mannitol, dithiothreitol, ATP disodium, ammonium molybdate, ascorbic acid, sodium meta-arsenite, aprotinin, leupeptin, EGTA, EDTA, HEPES, ouabain, phenylmethylsulfonyl fluoride, and TRIZMA base were purchased from Sigma Chemical Co. (St. Louis, Mo.). Hanks' balanced salt solution, Alpha Minimum Essential Medium, DMEM, penicillin/streptomycin, fetal bovine serum (FBS), and trypsin-EDTA were obtained from Life Technologies, Inc. (Rockville, Md.). Sodium orthovanadate was purchased from Pfaltz & Bauer Inc. (Waterbury, Conn.). Microplates (Costar 96-well), plastic tubes, and cell culture flasks (75 cm$^2$) were purchased from Corning Inc. (Corning, N.Y.). All other reagents were of the highest grade commercially available.

CR1R12 cell line, provided by the University of Rochester, was maintained as described previously. Wang E-J, et al. (2000a) *Drug Metab Disp* 28:522–528. The 3T3 G185 cell line presenting the gene product of human MDR1 was licensed from NIH and maintained in DMEM.

A direct functional assay was performed with the FACS flow cytometer as described previously. Ibid. The consumption of ATP was determined by the liberated inorganic orthophosphate, which forms a color complex with molybdate. Wang E-J, et al., (2000b) *Biochimica Biophysica Acta* 1481:63–74.

RESULTS

Figure 2:
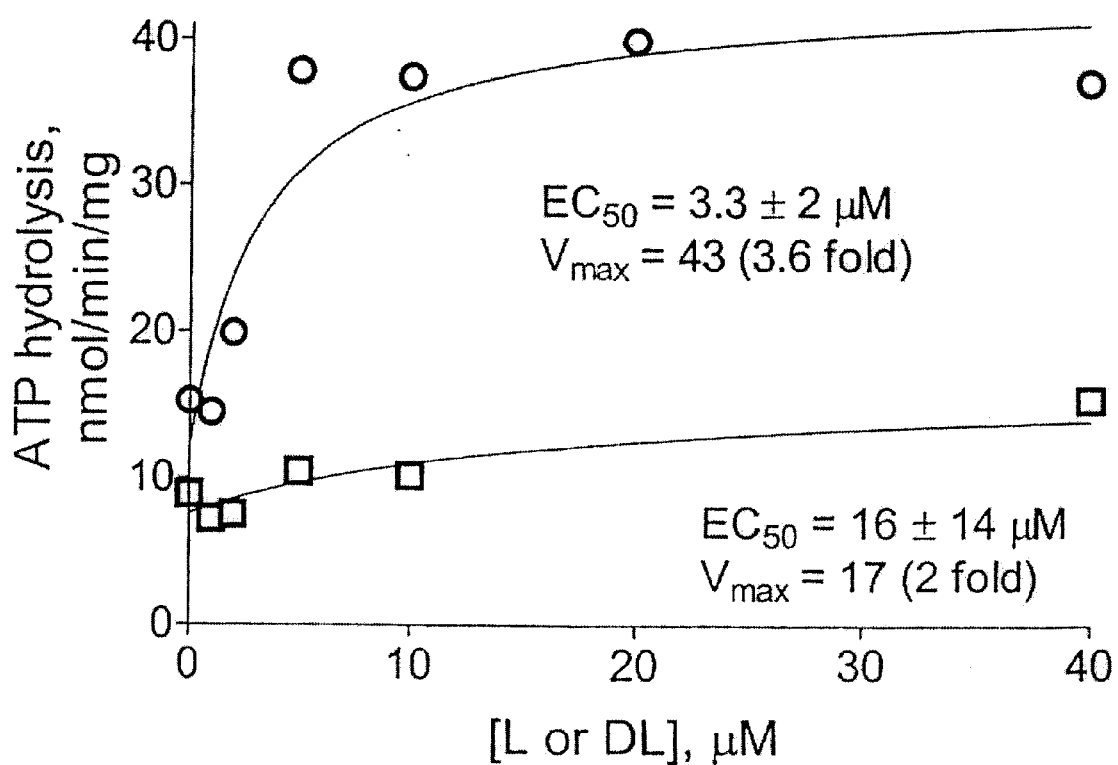
FIG. 2 depicts the inhibition of loratadine relative to desloratadine.

Inhibition of function was measured as such:
FIG. 1 depicts the Intracellular retention of daunorubicin in G185 cells versus competing verapamil (a; squares), cyclosporine A (a; circles),
FIG. 2 depicts loratadine (b; circles), and desloratadine (b; squares) concentration.

Fluorescence intensity is expressed as relative fluorescence. The efflux phase or incubation was 30 minutes in all cases. The average number of cells per assay was 10,000. The function for the line through the data is the Hill equation: $v=V_{max}S^n/(K'+S^n)$. The parameters $IC_{50}$ and the maximum inhibition ($I_{max}$) along with the standard deviation are shown on the respective graphs.

Figure 3:
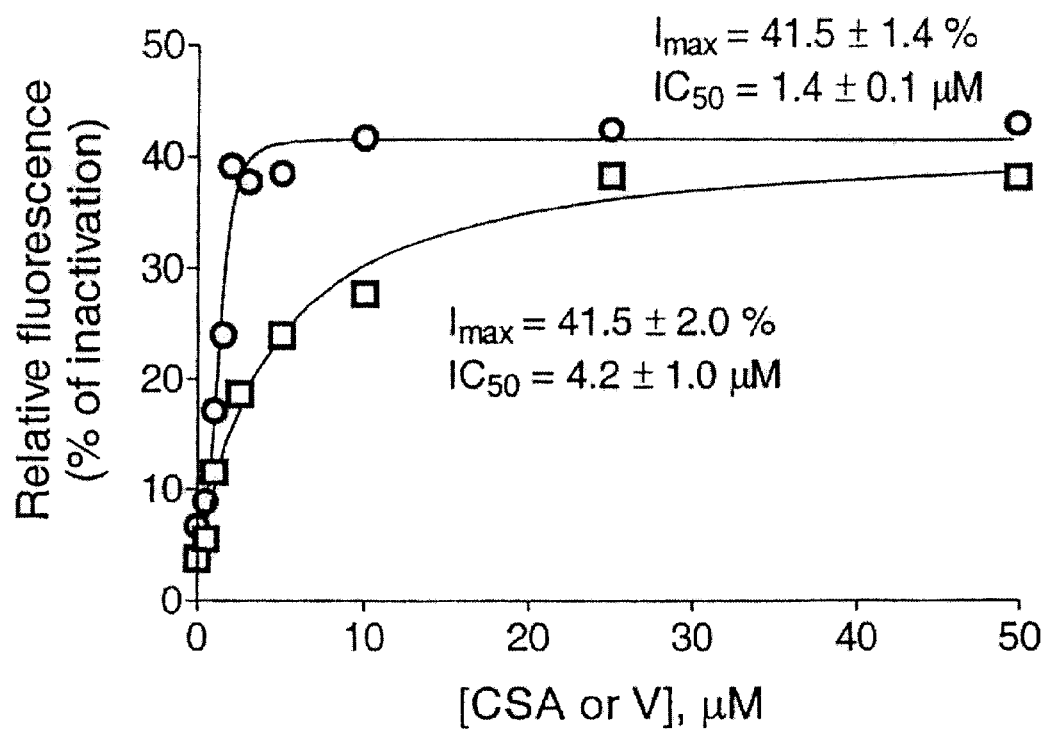
FIG. 3 depicts the activity of loratadine versus desloratadine by the respective rates of P-gp mediated ATP hydrolysis.
Figure 4:
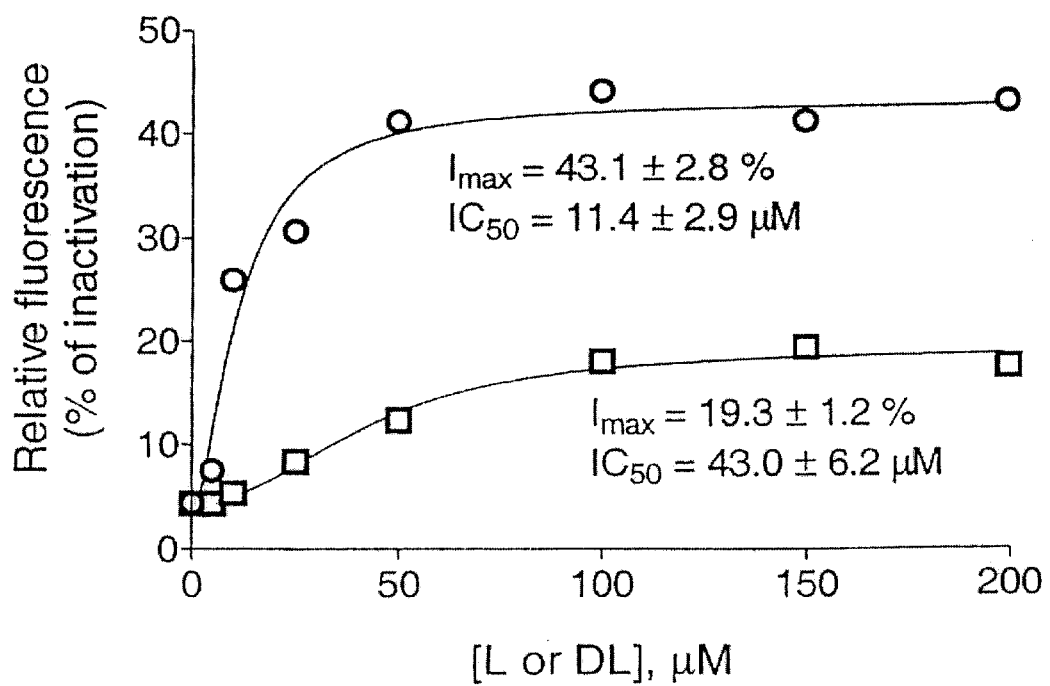
FIG. 4 depicts the activity of loratadine versus desloratadine by the respective rates of P-gp mediated ATP hydrolysis.

Activity was measured as such:
FIG. 3 depicts P-gp-mediated ATP hydrolysis rates versus loratadine (circles) or desloratadine (squares) concentration. The data for loratadine is fit to a hyperbola and the $V_{max}=48\pm7$ nmol/min/mg membrane protein with a $K_m=3\pm1.7$ µM.
FIG. 4 depicts P-gp-mediated ATP hydrolysis rates versus loratadine or desloratadine in the presence of 10 µM H33342 (to lower the baseline activity). The data is fit to a hyperbola and for loratadine (circles) the $V_{max}=42\pm7$ nmol/min/mg membrane protein with an $EC_{50}=3.3\pm2$ µM (instead of a parameter $K_m$ it is called an $EC_{50}$ for "effective concentration" as the conditions include an alternative substrate). For desloratadine (squares) the $V_{max}=17\pm4$ nmol/min/mg membrane protein with an $EC_{50}=16\pm14$ µM.

INHIBITION OF FUNCTION

Inhibition of marker efflux was employed in this study to characterize the interaction potential of loratadine, desloratadine, and some known substrates with MDR1. Wang E-J, et al. (2000a) *Drug Metab Disp* 28:522–528. Vanadate, a known, very potent inhibitor of MDR1 efflux function, served as a positive control. Inclusion of adequate concentrations of vanadate in the incubation media inhibited daunorubicin efflux dye and resulted in a dramatic increase in retained fluorescence. This condition was considered to represent total inhibition.

Loratadine caused a concentration-dependent increase in fluorescence retention during the efflux phase. Maximum inhibition by L was approximately 43% of that observed with vanadate (total inhibition). The concentration dependency of inhibition displayed a sigmoidal response curve (FIG. 1), a consequence of ooperativity, with the Hill equation for allosteric interaction therefore providing a ignificantly better fit to the data: $v=V_{max}S^n/(K'+S^n)$. Wang E-J, et al., (2000 c) *Arch Biochem Biophys* 382(2):91–98. The $IC_{50}$ for L in the NIH 3T3-G185 cell line (overexpressing the cloned human MDR1 gene product) on this passage was ~11 µM, less potent than the positive controls, verapamil and cyclosporin A (FIG. 1) with an $IC_{50}$ of about 4 µM and 1 µM, respectively. For loratadine the $IC_{50}$ was ~160 times the maximum observed plasma concentration ($C_{max}$) following the recommended dose of 10 mg. Salmun L., et al., (2000) *Clin Ther* 22:573–583.

Desloratadine caused significantly less functional inhibition, achieving a maximum equivalent to only 19% total inhibition (FIG. 2). Moreover, the $IC_{50}$ of ~43 µM was about fourfold greater than that for loratadine. For desloratadine, the $IC_{50}$ was ~880 times the maximum observed plasma concentration ($C_{max}$) following the recommended dose of 5 mg. Banfield, et al., 2001 (In Press). The results described here using cells with the human MDR1 transporter are similar to those using a rodent cell and transporter.

ACTIVITY

If a compound is a substrate of P-gp the hydrolysis of ATP is required as the driving force. As ATP is consumed at a purported rate of about one or two per transport event, the hydrolysis of ATP represents transport rate or activity assay of function. As exemplified by the known P-gp substrate nifedipine, there was a clear concentration dependency with activity rising to a maximum at ≈44 nmol/min/mg (positive control, not shown). By fitting the data to a modified form of the Michaelis-Menten equation (added constant accounting for baseline activity) using nonlinear regression, a $K_m$ of about 13 μM and a $V_{max}$ of about 240% of control activity was determined. It was noted that in the absence of a substrate, the enzyme was able to hydrolyze ATP to produce a basal level of phosphate release. Therefore, activity data are presented as a percent of the basal or control activity that is probably due to the transport of endogenous substrate(s). Any change in the rate of ATP hydrolysis represents the sum of the basal activity and the contribution of the exogenous substrate to ATP hydrolysis. Therefore, a substrate with a rate similar to basal activity may not exhibit altered ATP hydrolysis activity due to masking by the basal activity. As often reported, known substrates of P-gp have demonstrated a clear repeatable concentration-dependent increase in ATP hydrolysis activity.

As shown in FIG. 3, loratadine caused an increase in ATP hydrolysis activity above basal levels with a classic Michaelis-Menten relationship to concentration. Loratadine appears to be a faster substrate (transport rate higher than many other substrates) with a $V_{max}$ that is ≈200% above basal activity and a $K_m$ of 3 μM. Desloratadine has no significant effects on ATP hydrolysis under the conditions of the assay (FIG. 3). Since the transporter exhibits basal activity, however, the addition of an exogenous transporter substrate may not change the ATP hydrolysis rate if its rate of transport is similar to the basal rate. The Hoechst compound H33342, known to reduce ATPase activity below basal activity, was used to reveal effects on ATP hydrolysis that would otherwise be masked by basal activity. For example, repeating the above experiments in the presence of 10 μM H33342 (for all assays) lowers the basal activity and changes the assay or baseline reference point. Under these conditions, loratadine increases ATP hydrolysis rates with an $EC_{50}$ (as conditions are contrived, the parameter is designated $EC_{50}$) similar to the $K_m$ determined under assay conditions without H33342 added (FIG. 4). Desloratadine caused a slight increase in hydrolysis above the suppressed (with 10 μM H33342) activity; this increase occurred, however, only at very high concentrations when compared to loratadine (FIG. 4). The interaction of desloratadine with P-gp is fourfold less than that of loratadine, a result in agreement with the comparative results from the direct transport inhibition in whole cell described above.

Here, we show by two different methods that the interaction of desloratadine with the ubiquitous ABC transporter P-gp is significantly less than that of loratadine, a widely prescribed antihistamine with a prodigious safety record. This result supports some structure activity relationship studies showing that less lipophilic (hydrophobic) compounds are often less likely to interact with the substrate binding site of P-gp. As desloratadine is the descarboethoxy oxidized loratadine, it is less lipophilic—and hence more soluble—and would therefore be expected to have a lower affinity for the binding site of the MDR1 gene product, P-gp. Indeed, the functional inhibition of P-gp by desloratadine was much less than that by loratadine, as measured by both extent and affinity (4 fold) despite suggestions of a significant interaction with P-gp. See Hwang K, et al., (2000) *J Clin Pharmacol* 40(9):1060. In other words, the maximum extent of desloratadine-mediated inhibition was still less than half that achieved by other positive compounds including loratadine. Moreover, loratadine itself, with an $IC_{50}$ of about 11 μM, would not be expected to exhibit significant interactions at clinically relevant doses, which indeed is the case. The $IC_{50}$ values represent about 160 times the highest observed $C_{max}$ of loratadine and 880 times the highest observed $C_{max}$ of desloratadine. Hence, desloratadine would be expected to exhibit no clinical interaction with compounds transported by P-gp even at the higher concentrations expected in intestinal mucosal. Indeed, clinical studies show that desloratadine exhibits no significant interactions with typical test drugs. Banfield C., et al. (2001) Lack of Interaction Between Desloratadine and Erythromycin. *Clin Pharmacokinet*. In Press; Banfield C., et al., (2001) Desloratadine Has No Electrocardiographic or Pharmacodynamic Interactions with Ketoconazole. *Clin Pharmacokinet*. In Press.

The pharmacokinetic profiles of many drugs that are substrates for P-gp would therefore not be affected via this mechanism when co-administered with desloratadine. The lack of interaction with P-gp will mean more predictable pharmacokinetics of desloratadine when used in the treatment of allergic rhinitis and other allergic diseases.

What is claimed:

1. A method of treating and/or preventing allergic and inflammatory conditions of the skin or airway passages in a human in need of such treating and/or preventing which comprises administering to said human an effective amount of a nonsedating antihistamine for such treating and/or preventing while avoiding the side effects associated with other nonsedating antihistamines that bind to the P-glycoprotein pump and/or the organic anion transport polypeptide pump.

2. The method of claim 1, wherein the nonsedating antihistamine is desloratadine.

3. The method of claim 1, wherein the amount of the desloratadine is in the range of about 1 mg/day to about 20 mg/day.

4. The method of claim 1, wherein the amount of the desloratadine is in the range of about 1 mg/day to about 10 mg/day.

5. The method of claim 4, wherein the amount of the desloratadine is about 5 mg/day in single or divided doses.

6. The method of claim 4, wherein the amount of desloratadine is about 5 mg/day.

7. The method of claim 5, wherein the amount of desloratadine is about 2.5 mg/twice a day.

8. The method of claim 1, wherein the allergic and inflammatory condition is seasonal allergic rhinitis, perennial allergic rhinitis, atopic dermatitis, urticaria or allergic asthma.

9. The method of claim 1, wherein the other nonsedating antihistamine is fexofenadine.

10. The method of claim 1, further comprising administering a decongestant.

11. A method of treating and/or preventing allergic and inflammatory conditions of the skin or airway passages in a human of 12 years and older in need of such treating and/or preventing which comprises administering to said human an effective amount of a nonsedating antihistamine sufficient for such treating and/or preventing in the absence of the side effects associated with other nonsedating antihistamines that bind to the P-glycoprotein pump and/or the organic anion transport polypeptide pump.

12. The method of claim 11, wherein the nonsedating antihistamine is desloratadine.

13. The method of claim 12, wherein the amount of desloratadine is in the range of about 1 mg/day to about 20 mg/day.

14. The method of claim 13, wherein the amount of desloratadine is in the range of about 1 mg/day to about 10 mg/day.

15. The method of claim 14, wherein the amount of desloratadine is about 5 mg/day in single or divided doses.

16. The method of claim 15, wherein the amount of desloratadine is about 5 mg/day.

17. The method of claim 15, wherein the amount of desloratadine is about 2.5 mg/twice a day.

18. The method of claim 11, wherein the allergic and inflammatory condition is seasonal allergic rhinitis, perennial allergic rhinitis, atopic dermatitis, urticaria or allergic asthma.

19. The method of claim 11, wherein the other nonsedating antihistamine is fexofenadine.

20. The method of claim 11, further comprising administering a decongestant.

21. A method of treating and/or preventing seasonal or perennial allergic rhinitis in a human in need of such treating and/or preventing which comprises administering to said human an effective amount of desloratadine for such treating and/or preventing while avoiding the side effects associated with other nonsedating antihistamines that bind to the P-glycoprotein pump and/or the organic anion transport polypeptide pump.

22. The method of claim 21, wherein the amount of desloratadine is in the range of about 1 mg/day to about 20 mg/day.

23. The method of claim 22, wherein the amount of desloratadine is in the range of about 1 mg/day to about 10 mg/day.

24. The method of claim 23, wherein the amount of desloratadine is about 5 mg/day in single or divided doses.

25. The method of claim 24, wherein the amount of desloratadine is about 5 mg/day.

26. The method of claim 24, wherein the amount of desloratadine is about 2.5 mg/twice a day.

27. The method of claim 21, wherein the other nonsedating antihistamine is fexofenadine.

28. The method of claim 21, further comprising administering a decongestant.

29. A method of treating and/or preventing atopic dermatitis or urticaria in a human in need of such treating and/or preventing which comprises administering to said human an effective amount of desloratadine for such treating and/or preventing while avoiding the side effects associated with other nonsedating antihistamines that bind to the P-glycoprotein pump and/or the organic anion transport polypeptide pump.

30. The method of claim 29, wherein the amount of desloratadine is in the range of about 1 mg/day to about 20 mg/day.

31. The method of claim 30, wherein the amount of desloratadine is in the range of about 1 mg/day to about 10 mg/day.

32. The method of claim 31, wherein the amount of desloratadine is about 5 mg/day in single or divided doses.

33. The method of claim 32, wherein the amount of desloratadine is about 5 mg/day.

34. The method of claim 32, wherein the amount of desloratadine is about 2.5 mg/twice a day.

35. The method of claim 29, wherein the other nonsedating antihistamine is fexofenadine.

36. The method of claim 29, further comprising administering a decongestant.

37. A method of treating and/or preventing allergic asthma in a human in need of such treating and/or preventing which comprises administering to said human an effective amount of desloratadine for such treating and/or preventing while avoiding the side effects associated with other nonsedating antihistamines that bind to the P-glycoprotein pump and/or the organic anion transport polypeptide pump.

38. The method of claim 37, wherein the amount of desloratadine is in the range of about 1 mg/day to about 20 mg/day.

39. The method of claim 38, wherein the amount of desloratadine is in the range of about 1 mg/day to about 10 mg/day.

40. The method of claim 39, wherein the amount of desloratadine is about 5 mg/day in single or divided doses.

41. The method of claim 40, wherein the amount of desloratadine is about 5 mg/day.

42. The method of claim 40, wherein the amount of desloratadine is about 2.5 mg/twice a day.

43. The method of claim 37, wherein the other nonsedating antihistamine is fexofenadine.

44. The method of claim 37, further comprising administering a decongestant.

45. A method of treating the nasal and non-nasal symptoms of seasonal allergic rhinitis in a human of 12 years and older which comprises administering to said human an effective amount of desloratadine for such treating while avoiding the side effects associated with other non sedating antihistamines that bind to the P-glycoprotein pump and/or the organic anion transport polypeptide pump.

46. The method of claim 45, wherein the amount of desloratadine is in the range of about 1 mg/day to about 20 mg/day.

47. The method of claim 46, wherein the amount of desloratadine is in the range of about 1 mg/day to about 10 mg/day.

48. The method of claim 47, wherein the amount of desloratadine is about 5 mg/day in single or divided doses.

49. The method of claim 48, wherein the amount of desloratadine is about 5 mg/day.

50. The method of claim 48, wherein the amount of desloratadine is about 2.5 mg/twice a day.

51. The method of claim 45, wherein the other nonsedating antihistamine is fexofenadine.

52. The method of claim 45, further comprising administering a decongestant.

53. The method of claim 52, wherein the decongestant is pseudoephedrine.

54. A method of treating the nasal and non-nasal symptoms of seasonal allergic rhinitis in a human of 12 years and older which comprises administering to said human an effective amount of desloratadine for such treating while avoiding the side effects associated with the binding of fexofenadine to the P-glycoprotein pump and/or the organic anion transport polypeptide pump.

55. The method of claim 54, wherein the amount of desloratadine is in the range of about 1 mg/day to about 20 mg/day.

56. The method of claim 55, wherein the amount of desloratadine is in the range of about 1 mg/day to about 10 mg/day.

57. The method of claim 56, wherein the amount of desloratadine is about 5 mg/day in single or divided doses.

58. The method of claim 57, wherein the amount of desloratadine is about 5 mg/day.

59. The method of claim 56, wherein the amount of desloratadine is about 2.5 mg/twice a day.

60. The method of claim 54, further comprising administering a decongestant.

61. The method of claim 60, wherein the decongestant is pseudoephedrine.

62. A method of treating and/or preventing atopic dermatitis or urticaria in a human of 12 years and older in need of such which comprises administering to said human an effective amount of desloratadine for such treating while avoiding the side effects associated with the binding of fexofenadine to the P-glycoprotein pump and/or the organic anion transport polypeptide pump.

63. A method of treating and/or preventing the nasal and non-nasal symptoms of seasonal and perennial allergic rhinitis and for treating chronic idiopathic urticaria in a human of 12 years and older in need of such treating and/or preventing which comprises administering to said human about 5 mg of desloratadine once a day for about 10 days such treating while avoiding the side effects associated with the binding of fexofenadine to the P-glycoprotein pump and/or the organic anion transport polypeptide pump.

64. A method of treating and/or preventing the nasal and non-nasal symptoms of seasonal and perennial allergic rhinitis and/or of treating chronic idiopathic urticaria in a human of 12 years and older in need of such treating and/or preventing which comprises administering to said human an effective amount of desloratadine for such treating while avoiding the side effects associated with the binding of fexofenadine to the P-glycoprotein pump and/or the organic anion transport polypeptide pump.

65. A method of treating and/or preventing the nasal and non-nasal symptoms of seasonal and perennial allergic rhinitis and/or of treating chronic idiopathic urticaria in a human of 12 years and older in need of such treating and/or preventing which comprises administering to said human about 5 mg of desloratadine once a day for about 10 days such treating while avoiding the side effects associated with the binding of fexofenadine to the P-glycoprotein pump and/or the organic anion transport polypeptide pump.

66. A method of treating and/or preventing the nasal and non-nasal symptoms of seasonal and perennial allergic rhinitis and/or of treating chronic idiopathic urticaria in a human of 12 years and older in need of such treating and/or preventing which comprises administering to said human about 5 mg of desloratadine once a day for about 10 days such treating while avoiding the side effects associated with the binding of fexofenadine to the P-glycoprotein pump and/or the organic anion transport polypeptide pump.

67. A method of treating and/or preventing the nasal and non-nasal symptoms of seasonal and perennial allergic rhinitis in a human of 2 years and older in need of such treating and/or preventing which comprises administering to said human about 5 mg of desloratadine once a day for about 10 days of desloratadine in need of such treating while avoiding the side effects associated with the binding of fexofenadine to the P-glycoprotein pump and/or the organic anion transport polypeptide pump.

* * * * *